United States Patent [19]

Eilender et al.

[11] Patent Number: 4,572,174

[45] Date of Patent: Feb. 25, 1986

[54] LOW FRICTION BED PAD

[76] Inventors: Kasriel Eilender, 305 E. 86th St., New York, N.Y. 10028; Mille Stand, 2593 Sedgwick Ave., Bronx, N.Y. 10458

[21] Appl. No.: 554,260

[22] Filed: Nov. 22, 1983

[51] Int. Cl.[4] ........................ A61B 19/00; A47G 9/00

[52] U.S. Cl. ................................ 128/149; 128/132 R; 5/485; 206/438; 206/828

[58] Field of Search .................... 128/149, 132; 5/482, 5/484, 485, 487; 206/210, 438, 440, 441, 828

[56] References Cited

U.S. PATENT DOCUMENTS

| | | | |
|---|---|---|---|
| Re. 29,766 | 11/1978 | Wideman | 5/487 |
| Re. 30,972 | 6/1982 | Kyle et al. | 428/219 |
| 348,748 | 9/1886 | Kimball | 5/482 |
| 3,308,488 | 5/1965 | Schoonman | 5/500 |
| 3,574,873 | 4/1971 | Weinstein | 5/450 |
| 3,580,254 | 5/1971 | Stuart | 206/441 |
| 3,829,914 | 8/1974 | Treat | 5/81 R |
| 3,849,813 | 11/1974 | Neilson | 5/81 R |
| 4,097,943 | 7/1978 | O'Connell | 5/484 |

*Primary Examiner*—William R. Dixon, Jr.
*Assistant Examiner*—Karl Group
*Attorney, Agent, or Firm*—Anthony J. Casella; Gerald E. Hespos

[57] ABSTRACT

A bed pad structure is provided for the prevention of bed sores or pressure ulcers. The bed pad includes a pouch portion having an upper layer formed from a porous low friction material and a lower layer formed from a flexible impervious sheet material. The pouch portion is further constructed to enable easy insertion and removal of a lubricated insert in between the upper and lower layers. Lubrication from the insert can flow through the porous upper layer. The low friction characteristics of the upper layer plus the presence of the lubricant adjacent the patient substantially prevents friction and related wear which are contributing factors to the occurrence of bed sores.

14 Claims, 6 Drawing Figures

LOW FRICTION BED PAD

BACKGROUND OF THE INVENTION

It is well established that recent medical advances have resulted in longer life expectancies. These changes in life expectancy when coupled with changes in population levels have yielded a population of elderly people that is much greater than ever before. For example, it is estimated that in 1902 about 2 million people in the United States were at least 65 years old. The latest census, however, reveals that approximately 24 million people in this country are at least 65. It is expected that this trend will continue.

Despite the ability to keep people alive longer, the human body still undergoes substantial changes as part of the aging process. The changes which are attributable to aging include changes to the capillaries in and near the skin, changes to the muscles and tissues below the skin, and changes to the resiliency of the skin. As a result of these changes in and near the surface of the skin, an elderly person who is confined to bed for an extended period of time is likely to develop the decubitus ulcers or pressure ulcers which are commonly known as bed sores. Bed sores are an ancient problem which recently have begun to reach catastrophic proportions due to the growing number of elderly people.

Bed sores are open ulcerations which generally appear in the skin which covers a bony prominence. Additionally, bed sores typically occur at weight bearing parts of the body. Since bed sores are most prominent among bed ridden or wheelchair ridden elderly patients the ulcers are most likely to appear on portions of the back which overlie prominent bones. For example in "Pressure Ulcers: Prevention and Treatment", *Clinical Symposia,* Vol. 31, no. 5, 1979, Agress and Spira estimate that 23% of bed sores occur adjacent the sacrum or lower spine, 24% are located at the base of the buttocks; 15% are located at the trochanter, which is located on the thigh bone in the vicinity of the hip; 8% are at the back of the heel; 7% at the ankle; 6% at the knees; 4% at the iliac crest, which is the front bony pretrusion of the hip; 3% at the elbows and 2% at the pretibial crest which is directly below the knee. Other significant areas of occurrence include the base of the skull, the chin and upper and lower portions of the back.

Bed sores often are analogized to icebergs in that only the tip of a large ulceration breaks through the skin. More specifically in most instances, the bed sore not only effects the upper layers of skin but also the underlying layers of fat and muscle and perhaps even the underlying bone. Bed sores are extremely difficult to treat, are very painful and have a major negative effect on the quality of life for bed ridden elderly people. As pointed out by Agress and Spira, in extreme instances, bacterial infection of the bed sore may be life threatening.

The name pressure ulcers implies that the principal source of bed sores is pressure. In fact the principal method for treating bed sores has been to eliminate or reduce pressure. For example many complicated and costly devices have been developed which effectively rotate patients periodically so that the weight bearing portions of the body are changed every few hours. Other devices and treatments have been developed to try to releave the pain and discomfort and to bring about healing of bed sores once they have occurred. These latter schemes have included the use of water beds, lambs' fleece and lambs' fleece treated with certain lubricating oitments and creams. None of these approaches have been very successful in either eliminating or treating bed sores.

It is now known that pressure is only one of several contributing factors which cause bed sores in elderly bed ridden patients. Other significant contributing factors include friction and heat. Friction is the resistance to sliding motion of two bodies pressed against one another. The general term friction encompasses static friction, which results from the resistance to motion in overcoming inertia, and dynamic friction, which is created by the irregularities of the two surfaces interlocked with one another. A significant force is required to overcome static friction and thus to obtain sliding movement of two bodies with respect to one another. Static friction ceases to be a significant factor after sliding momentum has been achieved between the two bodies. However dynamic friction manifests itself in the rubbing together of microscopic projections on the respective bodies. More particularly the dynamic friction caused by microscopic irregularities in all surfaces causes heat in proportion to the load and speed and effectively welds adjacent surfaces at their points of contact, resulting in tearing or galling.

When a soft material is pressed against a harder material and moved in sliding relation thereto, the softer material flows to conform to the topography of the hard material, thereby increasing the area of contact along with frictional forces and heat adjacent to the surface.

In general, a softer material wears faster than a harder material. Certain flexible materials such as the skin of a young person are quite elastic and will give when subjected to the forces of friction. However in older patients the skin is less elastic. Furthermore, if the skin of the older person is subjected to frequent frictional forces, it becomes even less elastic. If an elastic material, such as skin, has a hard backing, such as a bony protrusion under the skin, the natural elastic deformation of the skin is severely limited. The net result is that wear to skin will occur much more quickly in areas of skin which cover a boney prominence.

Wear of almost any surface subjected to friction is characterized by the removal of particles from the surface and by pitting. The loose removal particles causes further wear because of abrasion. Pitting of the surface further causes fatigue and weakening of the surface structure. Ultimately the wear attributable to friction eventually leads to fissures and cracks on the surface. Such faults if not treated immediately will grow because they are the weakest areas of the surface structure.

Accordingly, it is an object of the subject invention to provide a composite structure which substantially prevents bed sores.

It is another object of the subject invention to provide a composite pad structure with a very low coefficient of friction.

It is an additional object of the subject invention to provide a composite pad structure for preventing bed sores which can be placed between a patient and a supporting structure.

It is a further object of the subject invention to provide a composite pad structure for preventing bed sores which is comfortable to the patient and which cam be manufactured at a low cost.

It is yet another object of the subject invention to provide a composite pad structure which includes a low friction fabric and a lubricant.

SUMMARY OF THE INVENTION

The subject invention simultaneously employs a low friction fabric with a lubricant. Lubricants are materials which have an ability to deform or sheer in the direction of motion of surfaces sliding adjacent to the lubricant. Consequently when a lubricant is disposed between two adjacent moving surfaces, the surfaces ride on a film of the lubricant, and most wear will actually be localized to the lubricant.

The low friction fabric employed with the lubricant is a porous material having a coefficient of friction much lower than the coefficient of friction which normally occurs between skin and an adjacent surface of a bed sheet or clothing article. For comparison purposes, it is estimated that the coefficient of friction between human skin and a cotton sheet is approximately 0.6. The porous characteristics of the low friction fabric enables the lubricant to flow through the low friction fabric, and thereby further reduce frictional wear on the skin. The specific low friction porous fabric preferred for this invention is woven from PTFE coated material, such as the fabric woven from Teflon coated material and manufactured by W.L. Gore and Associates under the trademark Gortex. The coefficient of friction between PTFE and skin is approximately 0.04, which is less than 7% of the coefficient of friction betwen skin and cotton. Additionally, PTFE fabric is long lasting, flexible and has the required porous characteristics to enable an appropriate lubricant to flow therethrough.

The PTFE fabric, although naturally smooth, is not naturally lubricated. Therefore to achieve the desired lubricating characteristics it is necessary to place a source of lubrication adjacent to the PTFE fabric. In most instances this source of lubricant will be a flexible sheet material that is impregnated with a lubricating ointment or cream. Many known ointments or creams would be acceptable, and it is desireable in certain instances to further incorporate an appropriate medicant into the lubricating ointment or cream.

As noted above, a characteristic of any lubricant is that most wear that normally would occur on an adjacent surface will actually take place within the lubricant. Thus there is a gradual breakdown of the lubricating material. Additionally, to the extent that wear does occur on an adjacent surface, the sheared-off particles from the adjacent surface often are deposited in the lubricant. Furthermore, in the particular instance described above, part of the lubricant may be absorbed into or displaced by the skin disposed adjacent thereto. For the preceding reasons, it is important that the source of the lubricant be replaceable or replenishable. To ensure that the lubricant is not absorbed into the bed, wheel chair or other surface on which the patients weight is supported, it is preferred that an impervious sheet material be disposed between the source of lubricant and the bed, chair or other such structure.

This specific structure for carrying out the subject invention preferably comprises a flexible porous PTFE fabric disposed adjacent the patient, a flexible lubricant-impregnated pad or mat disposed adjacent the PTFE fabric and a non-porous impervious sheet material disposed adjacent the lubricant impregnated pad but on the side thereof opposite the PTFE fabric. It is preferred that the structure be manufactured such that the lubricant impregnated pad can be removed periodically and either recharged with additional lubricant or replaced entirely. This structure can be manufactured to cover the entire supporting surface of the bed, chair or the like. However, as noted above, bed sores typically occur only adjacent areas of the body where a bony protrusion is disposed near the surface of the skin. In view of this predictable and localized occurrence of bed sores it is possible to make smaller composite pad structures which are affixed to the bed, chair or the like adjacent the areas of the patient where bed sores would be anticipated.

In a preferred embodiment the low friction composite pad structure includes attachments which enable the pad to be affixed to the supporting structure in a replaceable but substantially stationary manner. For example in one particular embodiment, as explained and illustrated below, the bed pad includes a plurality of straps which can be wrapped around the supporting structure and connected to one another.

DETAILED DESCRIPTION OF THE PREFERRED EMBODIMENT

Figure 1:
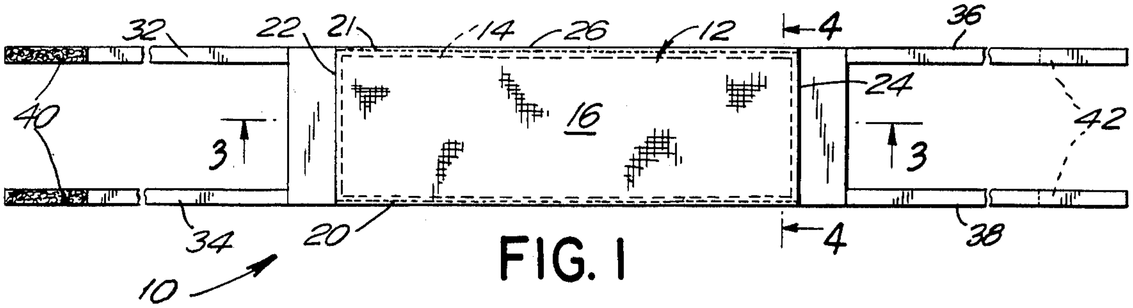
FIG. 1 is a plan view of the bed pad of the subject invention.
Figure 2:
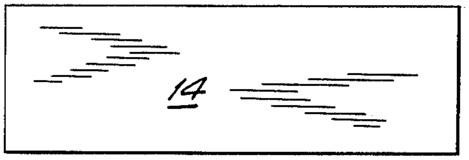
FIG. 2 is a plan view of the lubricant impregnated insert of the subject invention.

The pad of the subject invention is indicated generally by the numeral 10 in FIG. 1. The pad 10 is a composite structure which includes a pouch portion 12 into which a lubricated insert 14 is placed. The lubricated insert 14, as shown most clearly in FIG. 2, is a substantially rectangular piece of flexible sheet material which is impregnated with a lubricating ointment or cream. In addition to being impregnated with the lubricant, the insert 14 may also be treated with medications as appropriate.

Figure 3:
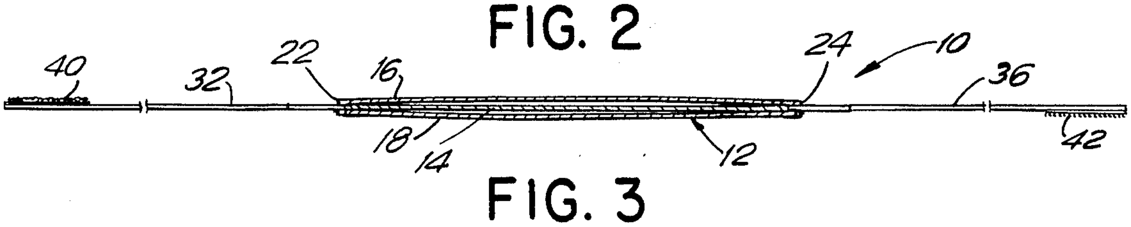
FIG. 3 is a cross-sectional view taken along lines 3—3 in FIG. 1.
Figure 4:
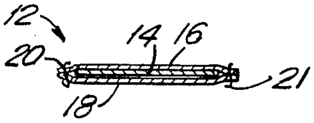
FIG. 4 is a cross-sectional view taken along lines 4—4 in FIG. 1.

With reference to FIGS. 1 and 3, the insert 14 is dimensioned to fit entirely within the pouch 12. The pouch 12 is of generally rectangular planar configuration, and is formed from an upper layer 16 and a lower layer 18. More particularly, the upper layer 16 is a low friction porous sheet material which preferably is formed from a woven PTFE fabric. The PTFE fabric employed in the upper layer 16 preferably is woven Teflon coated fabric sold by W.L. Gore and Associates under the trademark Gortex. As noted above, this PTFE fabric has a coefficient of friction of approximately 0.04. Additionally the porous characteristics of the PTFE fabric from which the upper layer 16 is formed enables the lubricant of the insert 14 to permeate through the upper layer 16, thereby further reducing friction between the skin of the patient and the pad 10. The lower layer 18 of the pouch portion 12, as shown in FIGS. 3 and 4, is formed from an impervious flexible sheet material such as a plastic sheet or a woven fabric of plastic coated fibers.

The upper and lower layers 16 and 18 are fixedly secured to one another along longitudinal seams 20 and 21. The longitudinal seams 20 and 21 may either be formed by stitches or in certain instances by heat sealing. The upper layer 16 has opposed ends 22 and 24. One of the ends 22 and 24 may either be stitched or heat sealed to the lower layer 18. However at least one end 22 or 24 is free of the lower layer 18 to define an opening which enables insertion or removal of the lubicated insert 14. With this particular construction, a closure device may be disposed adjacent an end 22 or 24, as explained below without imposing any discomfort to a patient lying on the subject pad 10.

The bed pad 10, as shown in FIGS. 1 and 3, further includes straps 32, 34, 36 and 38 which are securely attached to the pouch 12. The straps 32 through 38 are of sufficient length to be extended substantially around the structure on which the patient is supported. As shown in the FIG. 6, the straps 32 through 36 are provided with releasable fastening mechanism 40 and 42 such as those sold under the trademark Velcro.

Figure 5:
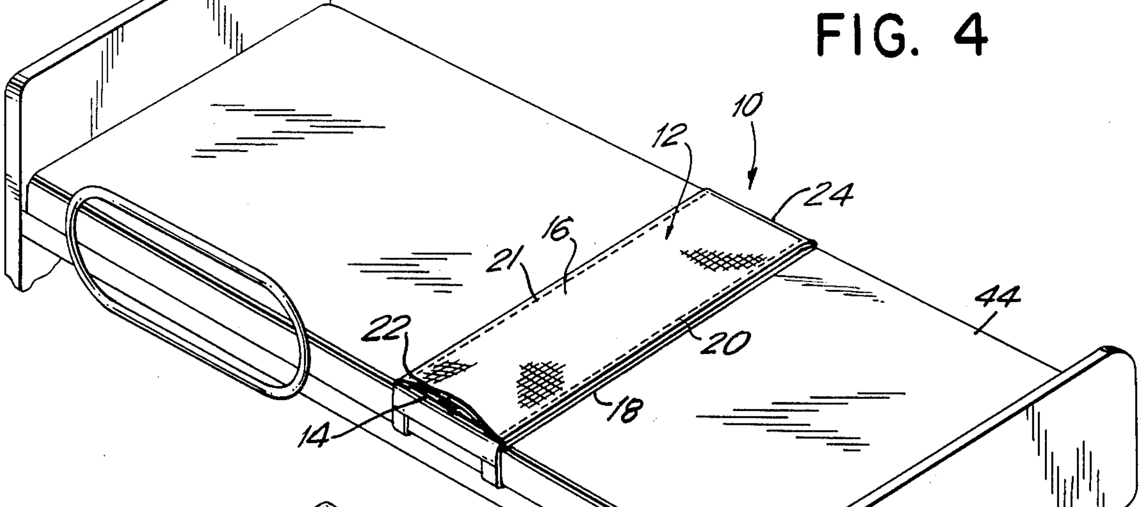
FIG. 5 is a perspective view of the pad of the subject invention positioned on a bed.
Figure 5:
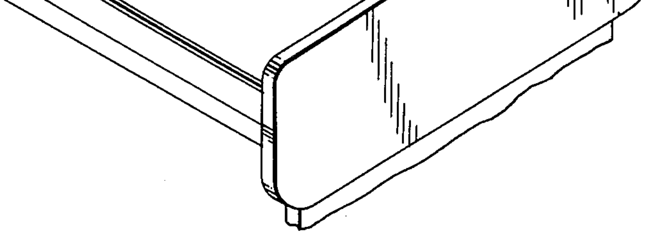

In use, the pad 10 is securely mounted to a supporting structure such as a bed 44. More particularly, the straps 32, 34, 36 and 38 are respectively wrapped around the bed 44 or other supporting structure and are secured to one another at the fastening mechanisms 40 and 42. The pad 10 is positioned on the bed 44 to be substantially aligned with a portion of the patient's body which is particularly susceptible to bed sores. As illustrated in FIG. 5, for example, the pad 10 is positioned to be substantially in line with the buttocks portion of the patient. In some instances it may be desireable to employ more than one such pad, with other pads being positioned near the base of the skull, the rear portion of the heels, or the elbows. If the patient changes position, for example, from lying on his or her back to his or her front, the pad 10 can easily be repositioned on the bed 44 so as to be aligned with other areas of the body.

As explained above, and as illustrated clearly in FIG. 5, the lower layer 18, which is formed from an impervious sheet material is positioned against the surface of the bed 44. As a result of this positioning, the lubricant included in the lubricated insert 14 will not flow toward and be absorbed by the bed 44. Conversely, the upper layer 16 is formed from a porous material which readily allows the lubricant in the lubricated insert 14 to flow therethrough to further lubricate the interface between the patient and the surface on which he or she lies. Additionally, as explained above, the upper layer 16 is formed from a PTFE fabric which inheritantly has a very low coefficient of friction. Thus the combination of the low friction PTFE fabric from which the upper layer 16 is formed, and the ability of the lubricant from the lubricated insert 14 to flow through the upper layer 16 results in an extremely low coefficient of friction at the interface between the patient and the supporting surface. As explained in detail above, the low friction enabled by the subject bed pad 10 substantially prevents the onset of bed sores.

Figure 6:
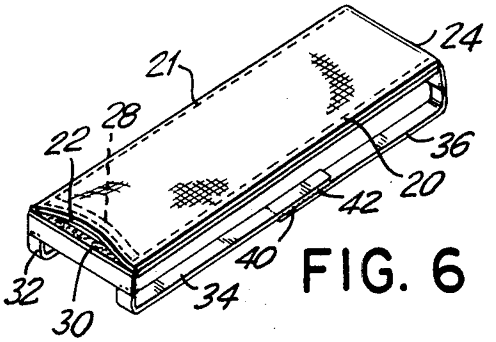
FIG. 6 is a perspective view of the bed pad of the subject invention.

FIGS. 5 and 6 also show the opening adjacent end 22 of top layer 16 in the pouch portion 12 which provides easy access to the lubricated insert 14 for the periodic replacement of the lubricated insert 14. To ensure secure closure of this opening, releasable closure strips 28 and 30, preferably Velcro, are mounted on the upper and lower layers 16 and 18 respectively. Since the closure strips 28 and 30 are at the very edge of the bed, they will not discomfort the patient.

In summary a composite pad is provided for substantially preventing bed sores. The pad includes an upper layer formed from a low friction porous material, a lower layer formed from an impervious sheet of flexible material and an insert impregnated with a lubricating ointment or cream to be placed between the upper and lower layers of the pad. Preferably the upper layers are formed from a porous PTFE fabric. In this construction, the pad is positioned on a bed or other supporting structure such that the upper layer is adjacent to the patient. The low friction characteristics of the upper layer substantially prevent the frictional wear and heat which are major contributing factors to the onset of bed sores. Additionally, the porous characteristics of the upper layer permits the flow of the lubricating cream or ointment to the area adjacent the skin of the patient, thereby further preventing bed sores. The bed pad includes straps or the like which enable the pad to be removably attached to the supporting structure. The pad is further constructed to enable periodic replacement of the lubricated insert. In use, the pad typically would be positioned strategically adjacent areas that are most succeptible to bed sores. However, larger sheets of the subject bed pad can be constructed to cover substantially an entire bed in accordance with the particular needs of the patient. Additionally, the subject structure can be incorporated into a clothing article to be worn by the patient.

While the invention has been described and illustrated with respect to a preferred embodiment, it is understood that various modifications can be made therein without departing from the spirit of the subject invention which should be limited only by the scope of the appended claims.

What is claimed is:

1. A composite pad for substantially preventing bed sores, said composite pad comprising:
   - an upper layer formed from a low friction flexible porous material;
   - a lower layer formed from a substantially impervious sheet material, said upper and lower layers being attached to one another to define a recloseable pouch therebetween; and
   - a lubricant disposed in said pouch, said lubricant being flowable through the porus upper layer thereby providing a low coefficient of friction between the upper layer and a skin surface adjacent thereto, whereby the low coefficient of friction substantially prevents bed sores on a patient supported on said upper layer of said composite pad.

2. A composite pad as in claim 1 wherein the lubricant is an ointment or cream.

3. A composite pad as in claim 1 further including a plurality of straps for releasably attaching the pad to a supporting structure.

4. A composite pad as in claim 1 wherein the upper and lower layers are substantially rectangular with said upper and lower layers each having two opposed pairs of edges, at least two said edges on said upper layer being fixedly attached respectively to the corresponding edges of said lower layer and with the remaining edges of said upper and lower layers being substantially free from one another to enable insertion or removal of the lubricant insert.

5. A composite pad as in claim 4 further including a releasable closure means adjacent said remaining edges for securely retaining the lubricant insert intermediate said upper and lower layers.

6. A composite pad as in claim 1 wherein the upper layer comprises a PTFE. material.

7. A composite pad as in claim 1 wherein the coefficient of friction between the upper layer and the patient supported thereon is about 0.04.

8. A composite structure for substantially preventing bed sores on the skin of a patient, said structure comprising:

a layer of porous sheet material characterized by the fact that the coefficient of friction between the porous material and the skin of the patient is approximately 0.04; and a substantially impervious layer of sheet material disposed adjacent said porous layer and affixed thereto so as to define a recloseable pouch therebetween for receiving additional material, whereby the positioning of said porous layer adjacent the patient reduces frictional wear on the skin of the patient thereby substantially preventing bed sores.

9. A structure as in claim 8 further including a lubricated sheet of material disposed in the pouch and intermediate said porous and impervious layers.

10. A structure as in claim 9 wherein the pouch includes a reclosable opening for insertion and removal of the lubricant impregnated sheet of material.

11. A structure as in claim 9 wherein the porous layer comprises a PTFE fabric.

12. A composite pad for substantially preventing bed sores on the skin of a patient, said composite pad comprising:

a porous upper fabric layer comprising PTFE; and an impervious lower layer, said lower layer being disposed adjacent said upper layer and being attached thereto to define a recloseable pouch therebetween.

13. A composite pad as in claim 12 further including a lubricated insert intermediate said upper and lower layers.

14. A composite pad as in claim 13 further comprising a plurality of straps secured thereto.

* * * * *